United States Patent [19]
Coody et al.

[11] Patent Number: 5,279,151
[45] Date of Patent: Jan. 18, 1994

[54] METHOD AND SYSTEM FOR CONDUCTING MESO-SCALE RAINFALL SIMULATIONS AND COLLECTING RUNOFF

[75] Inventors: Peter N. Coody; Lowell J. Lawrence, both of Lexington, Ky.

[73] Assignee: PTRL East, Inc., Richmond, Ky.

[21] Appl. No.: 789,932

[22] Filed: Nov. 12, 1991

[51] Int. Cl.$^5$ ............................................. G01N 17/00
[52] U.S. Cl. ...................................... 73/86; 73/863.52
[58] Field of Search ............. 73/7, 86, 863.31, 863.52, 73/865.4, 865.8, 866; 239/74, 211, 289, 71

[56] References Cited

U.S. PATENT DOCUMENTS

| | | |
|---|---|---|
| 3,934,472 | 1/1976 | Bradham . |
| 4,184,789 | 1/1980 | Gilde, Jr. . |
| 4,276,767 | 7/1981 | Cartwright ............................. 73/7 |
| 4,982,064 | 11/1934 | Norton . |
| 5,009,112 | 4/1991 | Lawrence et al. ............... 73/863.52 |

OTHER PUBLICATIONS

L. D. Meyer & W. C. Harmon, "Multiple-Intensity Rainfall Simulator for Erosion Research on Row Sideslopes", 1979, vol. No. 1, pp. 100–103.

Arthur E. Peterson & Gary D. Bubenzer, "Intake Rate: Sprinkler Infiltrometer", Methods of Soil Analysis, Part I. Physical and Mineralogical Methods–Agronomy Monograph No. 9, 2nd Edition 1986, pp. 845–870.

*Primary Examiner*—Robert Raevis
*Attorney, Agent, or Firm*—King & Schickli

[57] ABSTRACT

A method and apparatus are provided for conducting meso-scale rainfall simulations and runoff collections. The apparatus includes a system for continuously applying to a test plot simulated rainfall having a droplet size spectrum, an impact velocity, a spatial uniformity and an intensity simulating natural rainfall. Additionally, the apparatus includes a collector assembly for collecting runoff from the test plot for analysis. In accordance with the present method, natural rainfall for a geographic area including the test plot is studied in order to determine the drop size spectrum, drop impact velocity, spatial uniformity and intensity of the rainfall. A sprayer or irrigation head is then selected providing a droplet size spectrum closely resembling that of the natural rainfall to be simulated. Next, the spacing between and relative height of the irrigation heads is adjusted to ensure that the spatial uniformity, intensity and drop impact velocity resemble that of the natural rainfall to be simulated. The simulated rainfall is then continuously applied over the entire test plot. Next is the collecting of the runoff from the test plot and the analyzing of the runoff that is collected.

17 Claims, 3 Drawing Sheets

METHOD AND SYSTEM FOR CONDUCTING MESO-SCALE RAINFALL SIMULATIONS AND COLLECTING RUNOFF

TECHNICAL FIELD

The present invention relates generally to the environmental science field and, more particularly, to a method and apparatus for conducting meso-scale rainfall simulations and runoff collections for obtaining data on runoff water, pesticide runoff and sediment erosion from test sites.

BACKGROUND OF THE INVENTION

It has long been a desire of various environmental scientists, organizations and agencies to be able to complete effective studies or research relating to erosion and pesticide runoff such as occurs on agricultural fields or turf. For example, field studies designed to quantitate pesticide runoff and subsequent contamination of surface water need to be performed to obtain aquatic exposure assessments. Experience has, however, shown that pesticide runoff studies driven by natural rainfall are sometimes unsuccessful because the intense rainstorms typically required to provide useful data do not occur during the limited period of time when high pesticide residue levels remain in the field. The inherent risk associated with the weather dependent nature of these studies and the high cost of conducting experiments at multiple locations as needed to describe the runoff on a regional basis has led to the development of rainfall simulators adapted to complete the studies in a quick and cost effective manner.

In order to complete a valid study accurately reflecting what is naturally occurring in the environment, it must be appreciated that natural rainfall and, more particularly, natural rainfall as found in the particular geographic region under study needs to be simulated as closely as possible. This allows a "designed" rainstorm to be generated at any time after the pesticide is applied, thereby ensuring that the necessary weather conditions exist for a constructive study.

Attempts to accurately simulate natural rainfall began at least as early as the 1930's. The attempts to date have, however, met with only limited success. This is because the duplication of the rainfall characteristics of a natural storm is extremely difficult. In some instances the rainfall characteristics of geographical regions are not known in sufficient detail to allow accurate descriptions of the storms. In others, while the rainfall characteristics are known, it has been impossible up to the present time to develop a device capable of reproducing all desired characteristics. Accordingly, up to the present time complete rainfall simulation has not been possible. Accordingly, it has also not been possible to undertake completely accurate studies of erosion and pesticide runoff on anything other than small research plots of perhaps a few square meters.

A large number of natural rainfall characteristics or parameters must be considered in order to provide an effective simulation. This is particularly true as research has not as of yet clearly established the relative importance of the characteristics. Some of the characteristics that must be considered include: (1) the droplet size spectrum; (2) the droplet impact velocity with the ground; (3) the intensity/duration of the rainfall application; (4) the spatial uniformity of the droplet distribution over the test plot; and (5) the continuous application of the simulated rainfall over the entire test plot. Additionally, the expense of constructing, maintaining and operating a system must also be considered. Further, the portability of the system is important as on-site studies are absolutely essential and many sites are found in remote areas. It is also desirable to provide a simulation apparatus that may be quickly and efficiently reconfigured to simulate different natural rainfall such as may occur during a different season, in a different type of storm and/or in a storm from another geographic region.

One of the better rainfall simulators developed to date is disclosed in the article entitled "Multiple-Intensity Rainfall Simulator for Erosion Research on Row Side Slopes" by L. D. Meyer and W. C. Harmon reprinted from the transactions of the ASAE, 1979. This simulator includes oscillating spray nozzles to apply droplets of a size and at an impact velocity closely approximating natural rainfall.

Despite effectively simulating these two parameters, the device suffers from a number of shortcomings. More particularly, the oscillating spray nozzles only intermittently apply simulated rainfall over the test plot. This results in a non-uniform input of water and energy to the test plot over time unlike that associated with natural rainfall. The application of intermittent "rainfall" may significantly effect erosion patterns and pesticide runoff resulting in skewed data that lead directly to inaccurate conclusions.

It must also be appreciated that the design of the rainfall simulator in question only allows the application of the simulated rainfall over a relatively small test plot. The relatively small size of that test plot does not allow the collection of data that may be reasonably extrapolated to field-scale or meso-scale conditions. More particularly, a small test plot cannot support typical agricultural practices with respect to tillage and application using common farm equipment. This "tillage effect" is particularly significant because much of the water moving over a field is often conducted along the compacted tracks formed by modern farm machinery.

Further, while it is possible that a number of the apparatus in question could be positioned adjacent each other in a field to effectively provide a larger test plot, the viability of such a system is questionable. More particularly, the system would be very expensive to produce and operate. It would also be difficult to transport, arrange and effectively operate under field scale conditions. Further, the combined system would still rely upon oscillating spray nozzles for "rainfall" application. Thus, the drawbacks of intermittent energy input are not overcome. Accordingly, it should be appreciated that a need very clearly exists for an improved meso-scale or field-scale rainfall simulating apparatus particularly adapted to provide better simulations and accordingly, more accurate research data upon which to base study conclusions.

SUMMARY OF THE INVENTION

Accordingly, it is a primary object of the present invention to provide a method and apparatus for simulating rainfall and collecting runoff overcoming the above-described limitations and disadvantages of the prior art.

Another object of the present invention is to provide a rainfall simulation and runoff collection apparatus of relatively simple construction that is inexpensive to produce, maintain and operate.

An additional object of the present invention is to provide a meso-scale rainfall simulation and runoff collection apparatus that is convenient to utilize. More particularly, the device may be broken down and easily transported even to a remote location. Similarly, the device may be easily set up by as few as two people in a relatively short time.

Still another object of the present invention is to provide a method and apparatus for simulating rainfall and collecting runoff capable of accurately simulating rainfall over a large test area so as to provide data accurately reflecting erosion and pesticide runoff resulting from natural rainfall in the particular geographic area being investigated.

Still another object of the invention is to provide a method and apparatus for simulating rainfall and collecting runoff that may be easily adapted and reconfigured to simulate different rainfall such as natural rainfall commonly found in a different geographic region or rainfall from a different type of storm more commonly found during a different season in the geographic area under study.

Yet another object of the present invention is to provide a method and apparatus for simulating the droplet size spectrum, impact velocity, spatial uniformity and intensity of natural rainfall continuously over a large test plot area in order to provide better test results.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, an improved apparatus is provided for conducting meso-scale rainfall simulations and runoff collections. Broadly defined, the apparatus includes a means for continuously applying to a test plot simulated rainfall having a droplet size spectrum, an impact velocity, a spatial uniformity and an intensity similar to natural rainfall. Additionally, the apparatus includes a means for collecting runoff from the test plot for analysis.

More particularly, the means for applying simulated rainfall includes a pipeline for conveying water along the ground and a pump for pumping the water from a source through the pipeline. More particularly, the pipeline includes a main line running from the source through the pump to at least two lateral lines that preferably extend along the length of the test plot. Advantageously, by placing the main and lateral lines along the ground, the free flow of air and uninterrupted application of sunlight to the test plot is ensured. Accordingly, natural conditions are more accurately duplicated.

Riser lines are spaced at set intervals along the lateral lines. More particularly, the riser lines extend vertically upwardly between, for example, 3 to 15 feet with the upper or distal end of each line operatively connected to a spray means or irrigation head. The irrigation head includes a pressure regulator and a nozzle through which water is distributed over the test plot.

The type of nozzle selected for utilization in the irrigation head is determined by the droplet size spectrum characteristic of the natural rainfall to be simulated. The goal is to provide a droplet size spectrum as closely as possible corresponding to that of the natural rainfall being simulated.

The relative spacing between the lateral lines and the riser lines along the lateral lines is determined by the droplet distribution pattern of the selected nozzle when operating at the selected water pressure. The goal is to provide an even and continuous application or spacial uniformity of distribution characteristic of the rainfall to be simulated over the entire area of the test plot. Further, this is accomplished at an intensity level as similar as possible to that of the natural rainfall. Once again, the idea is to provide a simulated rainfall as closely as possible mimicking that of rainfall characteristic of that naturally received in the geographical area of the test plot. Of course, seasonal variations of rainfall for a particular geographical area may be taken into consideration. For example, a particular pesticide may be applied to a crop growing in the geographical area in question during the months of July and August. Ideally, rainfall typical of the geographical area for these particular months is simulated.

In order to insure that the simulated rainfall is properly applied, the apparatus also includes water pressure measuring devices in each of the lateral lines as well as a gate valve system for equalizing the water pressure in those lines. In this way, the system is ensured of operating at peak efficiency and performance at all times.

The runoff collecting means is more particularly described as a collector assembly. Preferably, the assembly includes an effectively continuous, impervious bottom wall that may, for example, be formed from sheet metal. Additionally, the collector assembly includes a retaining wall that abuts and defines a lower end of the test plot and a pair of upstanding sidewalls that converge as the sidewalls extend away from the retaining wall. Accordingly, a V-shaped collector assembly is provided with the wide end adapted for receiving runoff from the test plot. The converging sidewalls serve to concentrate the runoff as it moves downwardly along the sloping bottom wall toward a flume equipped with a means for measuring runoff flow.

After passing through the flume, runoff samples may be collected for further testing. Alternatively, a storage reservoir may be provided to hold the runoff from the test plot for further quantitative analysis. Preferably, the test plot covers an area of from 0.1 to 1.0 acres so as to include tillage effect and thereby ensure that the research data produced will accurately reflect actual erosion and runoff occurring in fields in the geographic region being studied.

In accordance with yet another aspect of the present invention, a method is provided for conducting meso-scale rainfall simulations and runoff collections. First, the natural intensity/duration of rainfall having a desired return frequency (e.g. one in ten year storm) in the test region is determined, for example, using published data. Next, the method includes a step of selecting a spray means or irrigation head providing a droplet size spectrum closely resembling the natural rainfall to be simulated. Additionally, the method includes the adjusting of the spacing between the irrigation heads in order to ensure spatial uniformity or even application of simulated rainfall over the test plot. Further, the adjusting of the relative height of the irrigation heads above the ground is completed in order to ensure that droplet velocity at time of impact with the ground closely resembles that of the natural rainfall being simulated. Next is the applying of the simulated rainfall evenly and continuously over the test plot at a selected rate or intensity for a selected period of time. This selected intensity is characteristic of natural rainfall in the area. Finally, the method concludes with the collecting of runoff from the test plot and the analyzing of the runoff that is collected.

In order to complete the most accurate research, it is also necessary to carry out studying natural rainfall for a geographic area including the test plot in order to determine the droplet size spectrum and droplet velocity at time of impact with the ground. Additionally, to ensure the best test results, the method should include the installing of a runoff collection assembly in the ground immediately adjacent a lower end of the test plot. In this way there is no buffer area of soil between the test plot and the runoff collection assembly. Alternatively, a buffer area of designed size and shape may be incorporated into the research being completed as desired. In order to achieve this end one performs the step of excavating the ground immediately adjacent the lower end of the test plot and then placing a runoff collection assembly of the type described above in the excavation. The runoff collection assembly is provided with an effectively continuous bottom wall that is impervious to the runoff and converging sidewalls for concentrating the runoff. In this way the runoff may be directed into a flume for complete and accurate analysis.

Still other objects of the present invention will become apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWING

The accompanying drawing incorporated in and forming a part of the specification, illustrates several aspects of the present invention and together with the description serves to explain the principles of the invention. In the drawing.

Figure 1:
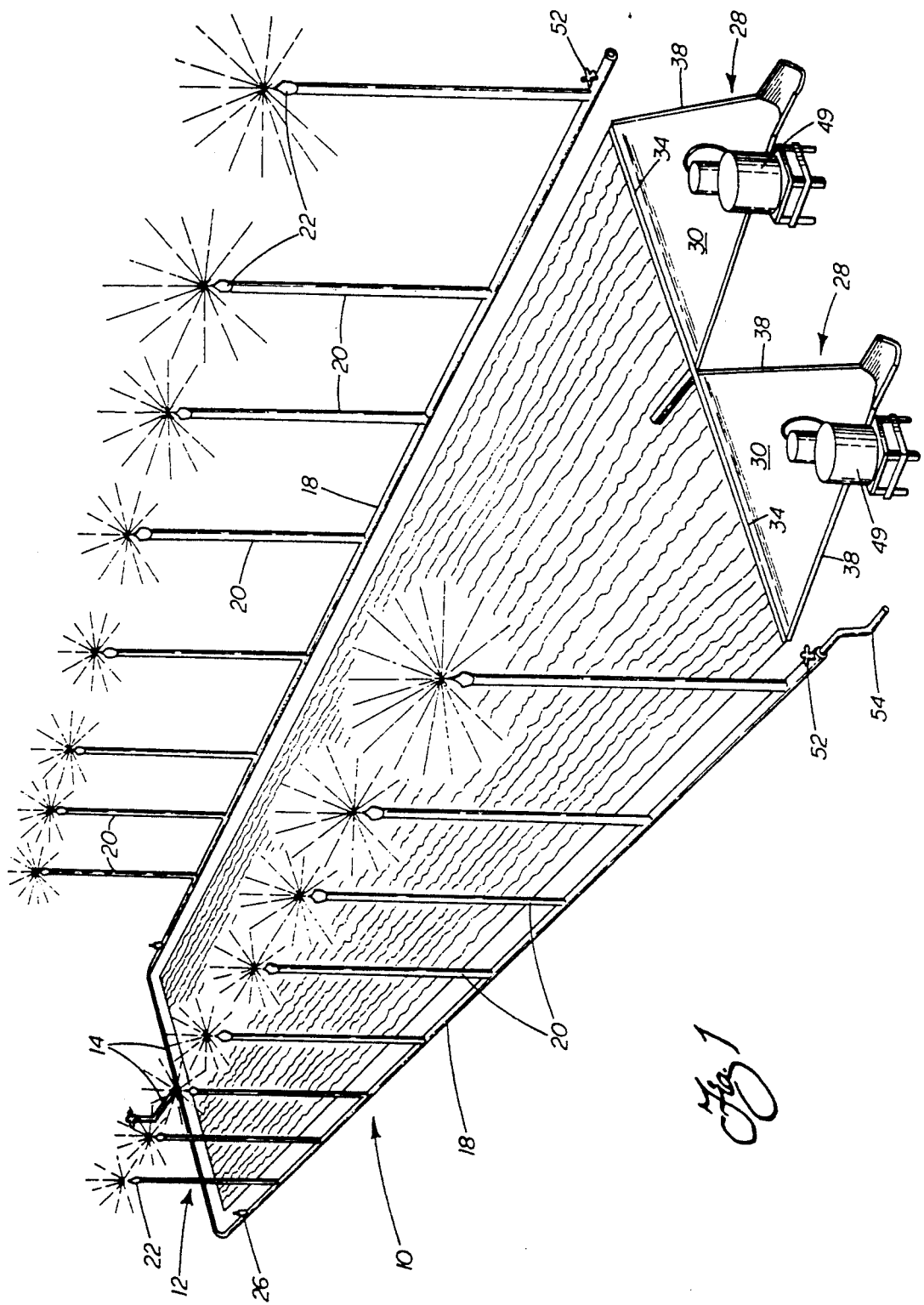
FIG. 1 is a perspective view showing the apparatus of the present invention for conducting meso-scale rainfall simulations and runoff collections.

Reference will now be made in detail to the present preferred embodiment of the invention, an example of which is illustrated in the accompanying drawing.

DETAILED DESCRIPTION OF THE INVENTION

Reference is now made to the drawing figures showing the apparatus 10 of the present invention for conducting meso-scale rainfall simulations and runoff collections from a test plot P. The apparatus 10 may, for example, be utilized for pesticide exposure assessment studies. Such studies may be conducted at one or more locations within the product use area (e.g. corn belt, cotton producing regions, principle apple producing states, etc.). The historical rainfall characteristics for the area are evaluated with respect to typical and extreme storms during the time of year when the product is in the field. A number of test plots, typically three to five, are tested per location. These test plots can be used to evaluate application methods such as broadcast versus incorporated, or to quantitate the runoff for different storm intensities and/or durations. Soil characteristics, including texture, organic matter, content, bulk density, water holding capacity, pH, cation exchange capacity and antecedent moisture are determined by depth within each runoff plot prior to the runoff event. These data may then be used to describe the runoff results as well as support eventual computer simulation modeling such as may be used to evaluate the environmental impact of pesticide use.

Figure 2:
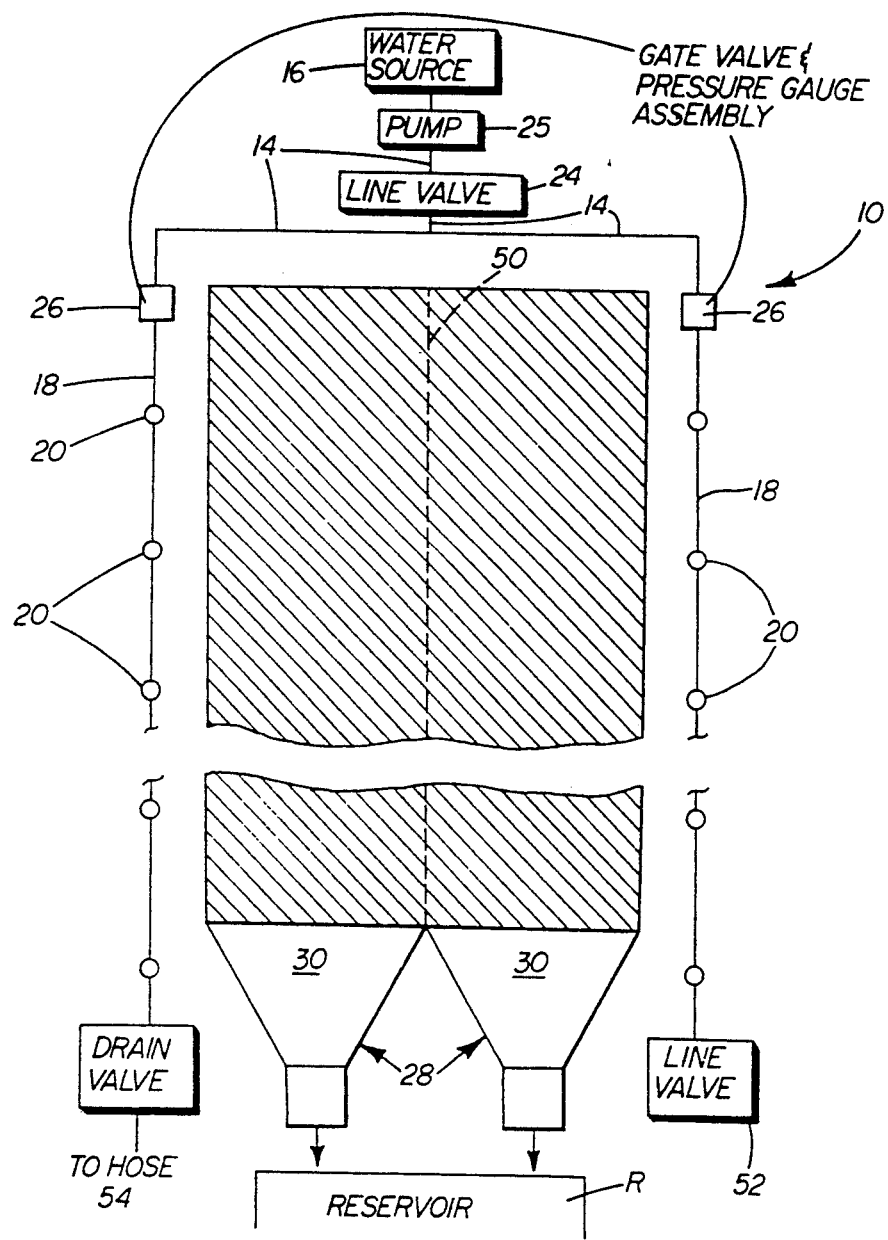
FIG. 2 is a schematical top plan view showing the apparatus of the present invention.
Figure 5:
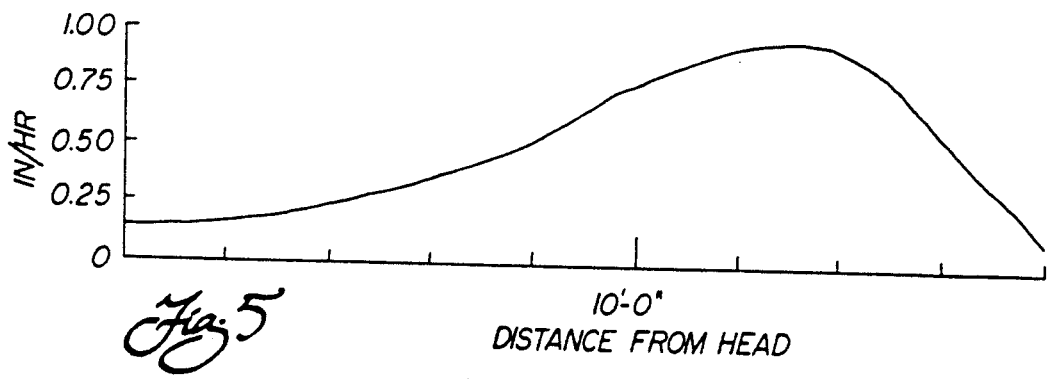
FIG. 5 is a graphical representation showing the radial droplet distribution profile of an irrigation head that may be used with the apparatus of the present invention.
Figure 3:
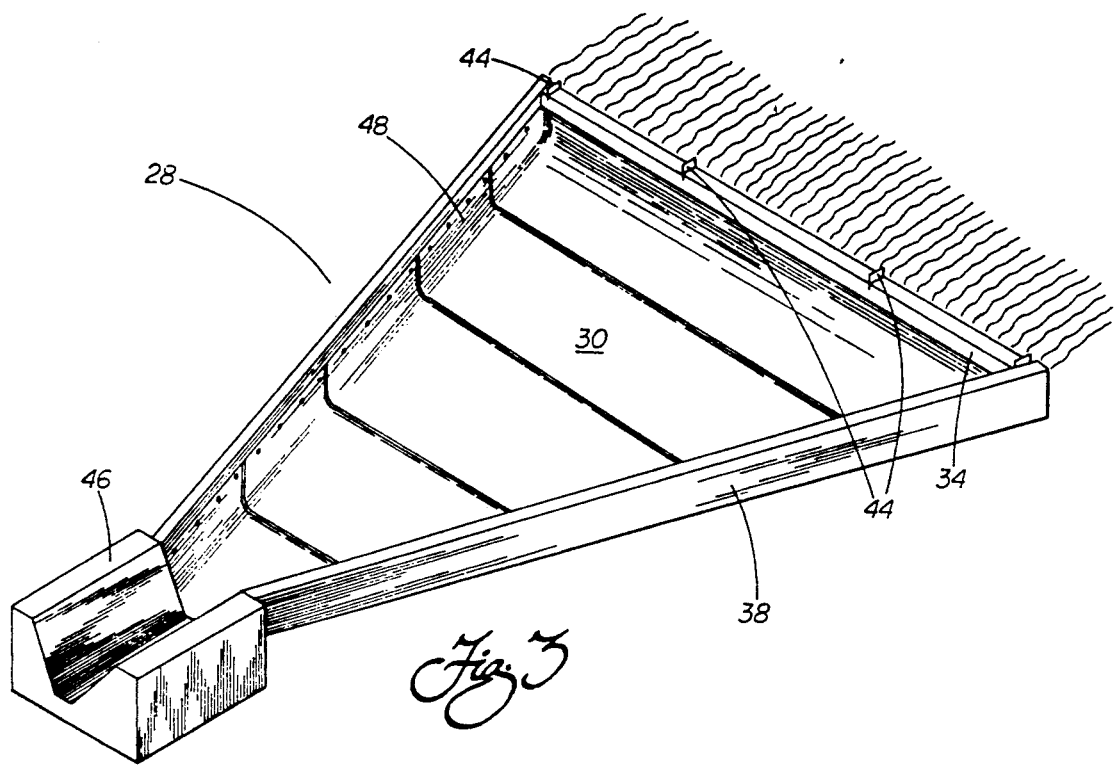
FIG. 3 is a detailed perspective view of the runoff collector assembly utilized in the apparatus of the present invention.
Figure 4:
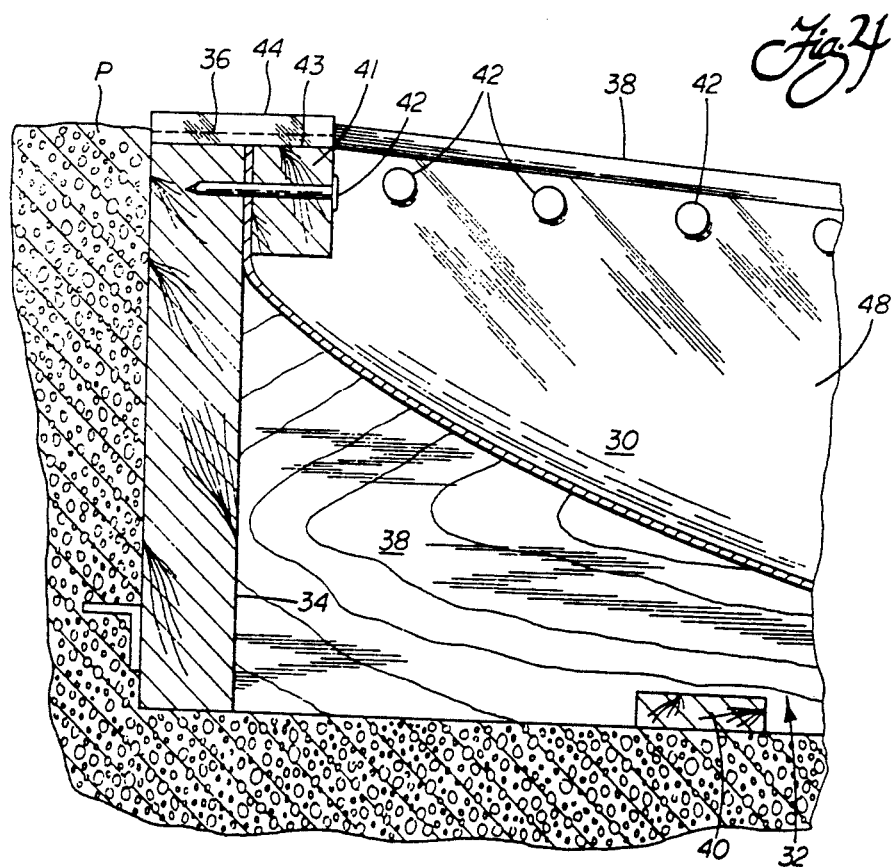
FIG. 4 is a detailed cross-sectional view showing part of the construction of the collector assembly.

As best shown in FIGS. 1 and 2, the apparatus 10 includes a system 12 for continuously applying simulated rainfall to the test plot P. The simulated rainfall has a droplet size spectrum and ground impact velocity similar to natural rainfall. These parameters are important because the total kinetic energy (KE) delivered by the raindrops is determined by the equation $KE = \frac{1}{2} mv^2$, where m=mass of the droplet and v=impact velocity. It is the kinetic energy delivered to the soil which is a key factor in causing soil detachment and eventual erosion.

Advantageously, the application system 12 also produces a simulated rainfall having an intensity and a spacial uniformity over the entire area of the test plot P substantially corresponding to that of natural rainfall. Accordingly, a uniform input of water and energy is provided over the test plot in the manner of natural rainfall. Accordingly, natural rainfall is more closely mimicked in the present system. As a result, erosion and pesticide runoff data more closely resembles that which actually occurs in the environment naturally.

More particularly, the simulated rainfall application system 12 includes a pipeline consisting of a header line 14 that provides water from a source 16 to two or more lateral lines 18. As shown, one lateral line 18 extends along the length of each side of the test plot P. A series of riser lines 20 are operatively connected to each lateral line 18 at spaced intervals. The spacing distance between the riser lines 20 and the height or heights of the riser lines are determined in a manner described in greater detail below so as to optimize natural rainfall simulation.

The upper or distal end of each riser line 20 is connected to an irrigation head 22. Each irrigation head 22 comprises a nozzle and pressure regulator. Advantageously, by providing a pressure regulator at each irrigation head 22, fluctuations in water pressure along the lateral lines 18 are accommodated so long as a sufficient back pressure is maintained. For example, the irrigation heads 22 may each comprise a Nelson Irrigation Corporation S-30 irrigation head with a #35 brass nozzle and a Nelson Irrigation Corporation pressure regulator of 10 or 15 psi. Additionally, a spinner plate such as a Nelson Irrigation Corporation D-4 plate of +8, −8, −18 and/or −45° may be selected to further tailor the droplet size spectrum and impact velocity to simulate natural rainfall.

As shown, water from the source 16 is fed through a control valve 24 in the header line 14 by means of a pump 25. The water then flows from the header line 14 into the two lateral lines 18. At the head of each lateral line 18, there is provided a pressure regulating gate valve and pressure gauge assembly 26. These assemblies 26 insure that the water pressure in the two lateral lines 18 is equalized and at the desired pressure to provide proper operation of the irrigation heads 22. Water in the lateral lines 18 is forced by the pump 25 through the riser lines 20 to the individual irrigation heads 22 where it is sprayed in a uniform pattern over the test plot P.

Advantageously, the application system 12 of the present invention is of relatively inexpensive construction such as PVC pipe sections. Accordingly, the system is relatively inexpensive to produce and may be constructed in various shapes and configurations so that a test plot P between, for example, 0.1 and 1 acre or greater in size may be selected. Such a test plot is large enough to support typical agricultural practices with respect to tillage and the application of farm equipment. Accordingly, test results may be more readily extrapolated to reflect actual full field effects relative to erosion and pesticide runoff.

Runoff from the test plot P may be readily collected in a runoff collector assembly 28 (note two shown at lower or downhill end of test plot in FIGS. 1 and 2).

As best shown in FIGS. 3 and 4, each V-shaped collector assembly 28 comprises a sheet metal collector, generally designated by reference numeral 30, held in a wooden support frame, generally designated by reference numeral 32. More particularly, each runoff collector assembly 28 includes a retaining wall 34 formed, for example, from a piece of 2×6 lumber. As best shown in FIGS. 1, 2 and 4, the ground adjacent the lower or downhill end of the test plot P is carefully excavated so as to not disturb the soil in the test plot. The retaining wall 34 is then placed in position so that the upper edge 36 is substantially level with the upper surface of the test plot P. An angle iron 37 or other flange may be provided on the retaining wall 34 and driven into the ground to help hold the retaining wall 34 in position. In the event such a flange 37 is provided, it is preferably positioned at least four inches below the top edge 36 of the retaining wall 34 so as to not disturb the upper layers of soil in the test plot P when the retaining wall is placed in position.

The remainder of the wood support frame 32 is then placed in position. This includes a pair of side rails 38 that converge toward one another as they extend from the retaining wall and a series of cross-braces 40 (only one shown in FIG. 4), spaced along and extending between the side rails to secure them in position. Of course, the various pieces of the support frame 32 may be fastened together by nails in a manner known in the art.

After the frame 32 is constructed, a sheet metal skin is attached to the frame so as to form the collector 30. More particularly, as best shown in FIG. 4, the sheet metal may be attached adjacent the upper edge of the retaining wall by means of a wood fastening strip 41 and nails 42. The upper edge of the fastening strip 41 is aligned with the upper edge 36 of the retaining wall 34 so that runoff flows freely down the slope of the test plot P over the retaining wall and fastening strip 41 into the collector 30. In order to ensure that runoff is not conducted laterally along the top edges of the retaining wall and fastening strip, a series of small transverse cuts 43 may be made. Metal flashing 44 is snugly positioned in these cuts 43. The flashing 44 acts as vanes to direct runoff flow to the collector 30.

The sheet metal forming the collector 30 may also be attached to each side rail 38 by means of nails 42. If more than one strip of sheet metal is required to form the collector 30, the upstream strip overlies the downstream strip so as to provide an overlap of approximately two inches. Accordingly, the collector 30 effectively provides a continuous, impervious bottom wall as the runoff from the test plot P flows downwardly on the sloped bottom wall to a flume 46. The slope is sufficient to ensure that sediment deposition as the runoff cascades down the collector 30 to the flume 46 is absolutely minimized. Of course, the converging sidewalls 48 of the collector 30 simultaneously concentrate and direct the flow for entry into the flume 46. A flow meter 49, such as an Isco Model 3230 bubbling flow meter may be utilized to monitor and measure the runoff as it passes through the flume 46. Further, the flow may be subsequently analyzed quantitatively for pesticide runoff if desired by taking periodic samples of the flow passing from the discharge end of the flume 46. Alternatively or additionally, flow from the flume may be directed to a storage reservoir R where the runoff flow may be held for further quantitative analysis.

The method for conducting meso-scale rainfall simulations and collections utilizing the apparatus 10 of the present invention will now be described. In this regard, an important step of the present method is the studying of the characteristics of natural rainfall for a given geographic area during an appropriate time of the year. By this it is meant that if it is desired to study the runoff of a pesticide utilized to treat apples in the area surrounding, for example, Spokane, Wash., typical and extreme storms historically occurring in this area during the summer and fall months will be studied. The goal is to determine the size spectrum of the droplets, the impact velocity of the droplets when they hit the ground and the intensity/duration of the rain. Once this information is ascertained, next is the selecting of an irrigation head providing a droplet size spectrum closely resembling the natural rainfall to be simulated. It is possible to do this by carefully selecting the nozzle, spinner plate and operating pressure of the irrigation head 22. For example, when working with an S-30 irrigation head from Nelson Irrigation Corporation, differing spinner plates may be selected to produce a unique droplet spectrum and projected droplet velocity. Accordingly, depending upon the type of natural rainfall to be simulated, Nelson Irrigation Corporation D-4 or U-4 plates of +8, −8, −18 and/or −45° may be utilized in the various irrigation heads 22 at the distal ends of the riser lines 20 in the application system 12.

Droplet impact velocities in a rainfall simulator are a function of the initial velocity when the drop leaves the nozzle under pressure and the acceleration/deceleration that occurs as the droplet falls to the ground. One approach for determining droplet velocities has been presented in the past by J. Otis Laws in an article entitled "Measurements of the Fall-Velocity of Water-Drops and Raindrops" reprinted from transactions of the American Geophysical Union, 1941. A summary table of velocities for sized droplets falling from a fixed height and including the inherent drag coefficients is included in this paper. The velocity of the water being sprayed from the nozzle may be measured as a function of droplet diameter utilizing known methods for this purpose. Using these data, a curve for the velocity may then also be plotted. This velocity is assumed to be the downward (Y-axis) initial velocity of the droplets leaving the irrigation head. A calculated actual velocity may then also be plotted. The calculated actual velocity (CV) as a function of droplet diameter is obtained as $CV = ((\text{measured velocity})^2 + (\text{fall velocity})^2)^{\frac{1}{2}}$. The calculated actual velocity curve demonstrates that droplets of the simulated rainfall have impact velocities closely approaching the terminal velocities of natural raindroplets. The tangential velocities may be more accurately calculated using the laws and formulae presented by I. D. Seginer in the article entitled "Tangential Velocity of Sprinkler Drops" published in *Transactions of American Society of Agricultural Engineers,* 1965.

Accordingly, it should be appreciated that it is possible to utilize this formula to closely match the droplet velocity of the simulated rainfall to the velocity of the natural rainfall being simulated. More particularly, the initial downward velocity of the droplets is considered and the relative heights of the riser lines 20 and irrigation heads 22 are adjusted until the desired impact velocity is achieved. Heights ranging anywhere from 3 to 15 feet may be utilized. For the taller heights, it is desirable to stabilize the riser lines 20 by tethering with a series of guide wires and stakes.

Droplet distribution or spatial uniformity of the simulated rain may also be matched to the natural rainfall being simulated. In the present apparatus 10, irrigation head placement is a function of the desired rainfall intensity. Thus, by design, the exact nozzle placement varies for each application. To ensure that water is applied to the test plot uniformly, each application will require that a "distribution analysis" be performed as a means of insuring good water coverage. Each spinner plate to be used in this system has a radial distribution profile determined such as that shown in FIG. 5. Such a profile represents a "fingerprint" of the water distribution around each nozzle in the system. Utilizing specially developed computer software presently available in the marketplace, it is possible to optimize the placement of the irrigation nozzles to achieve the maximum possible uniformity. The overall distribution can be characterized by the coefficient of uniformity (C.U.). An idealized uniform distribution of water around the test field has a C.U.=100%. During testing the present invention has achieved a C.U. of 94.9%. This indicates that excellent uniformity may be obtained with the present apparatus 10.

Accordingly, by selecting an irrigation head providing an appropriate droplet size spectrum, adjusting the spacing between the irrigation heads in order to ensure even application of rainfall over the test plot and adjusting the relative height of the irrigation heads to ensure an appropriate droplet impact velocity, natural rainfall may be closely simulated. This is particularly true using the apparatus 10 of the present invention wherein provision is also made for applying the simulated rainfall evenly and continuously over the entire test plot at a selected rate or intensity for a selected period of time. Accordingly, the actual energy of a natural rainstorm that drives the erosion and pesticide runoff is more closely mimicked to produce test data actually anticipating what occurs during a natural rainstorm.

The method also includes the additional step of collecting the runoff from the test plot. The collected runoff may then be analyzed qualitatively and/or quantitatively.

The following example is presented to further illustrate the invention, but it is not to be considered as limited thereto.

EXAMPLE 1

An apparatus was designed to apply simulated rainfall at a rate of 1.1 inch per hour to a test plot P of approximately 0.2 acres. The apparatus utilized the Nelson Irrigation Corporate S-30 irrigation heads with a Nelson U-4 +8° plate, a #35 brass nozzle and a 15 psi pressure regulator. Twenty-one irrigation heads were placed along two lateral lines located 43 feet apart. The irrigation heads were positioned at 14.9 foot intervals along the laterals (170 feet in length) and suspended to a height of 9 feet above the ground. A pressure gauge was installed at each lateral to measure the incoming water pressure (25–40 psi) and gate valving was included to equilibrate the pressure between the laterals as required. Water was supplied from a nearby pond by means of a 20 horse power pump. This apparatus 10 provided an artificial rainfall simulating an intense rainstorm in central Iowa having a return frequency of approximately one in five years.

In summary, numerous benefits have been described which result from employing the concepts of the present invention. Advantageously, the apparatus and method of the present invention very closely simulate the characteristics of natural rainfall including not only the drop size spectrum and impact velocity but also the spatial uniformity and intensity. Further, this is advantageously done in a system that is relatively simple to construct and easy to transport to and from the site. Additionally, the apparatus may be readily configured to provide rainfall characteristics simulating different types of storms or rainfall occurrences as may be found in another part of the country or at another period of time during the year in the same part of the country. Thus, the apparatus and method are flexible enough to be used across the country with relatively simple modification.

The foregoing description of a preferred embodiment of the invention has been presented for purposes of illustration and description. It is not intended to be exhaustive or to limit the invention to the precise form disclosed. Obvious modifications or variations are possible in light of the above teachings. For example, as shown in phantom line in FIG. 2, the test plot P may be divided by a wall 50 into two or more lanes to allow completion of separate pesticide studies simultaneously. Further, a drain valve 52 may be provided in the low ends of the lateral lines 18 to allow water to be easily released from the lines when preparing to break down or move the apparatus. Additionally, one of the valves may be operatively connected to a garden hose 54 (see FIG. 1). This hose may used by the operator to clean the collector assemblies 28 before runoff begins.

The embodiment was chosen and described to provide the best illustration of the principles of the invention and its practical application to thereby enable one of ordinary skill in the art to utilize the invention in various embodiments and with various modifications as is suited to the particular use contemplated. All such modifications and variations are within the scope of the invention as determined by the appended claims when interpreted in accordance with breadth to which they are fairly, legally and equitably entitled.

We claim:

1. A system for conducting meso-scale rainfall simulations and runoff collections, comprising:
   means for evenly and continuously applying to a test plot simulated rainfall having a droplet size spectrum, an impact velocity, a spatial uniformity and an intensity/Duration similar to natural rainfall whereby a substantially uniform input of water and energy is attained over said test plot; and
   means for collecting runoff from said test plot for analysis, said runoff collecting means including a collector assembly having a continuous, impervious bottom wall, a retaining wall abutting and defining a lower end of the test plot and a pair of upstanding sidewalls that converge as said sidewalls extend away from said retaining wall.

2. The apparatus set forth in claim 1, wherein said simulated rainfall applying means includes pipeline means for conveying water along the ground and means for pumping water through said pipeline means.

3. The apparatus set forth in claim 2, wherein said pipeline means includes a main line and at least two lateral lines,, said main and lateral lines running along the ground so as to allow the free flow of air and an uninterrupted application of sunlight to the test plot.

4. The apparatus set forth in claim 3, wherein said simulated rainfall applying means further includes spaced riser lines extending vertically upwardly from said at least two lateral lines and spray means operatively mounted to a top end of said riser lines.

5. The apparatus set forth in claim 3, including means for measuring water pressure in each of said at least two lateral lines and valve means for equalizing the water pressure in said at least two lateral lines.

6. The apparatus set forth in claim 1, wherein said retaining wall includes a horizontally extending flange that is inserted into the ground beneath the surface of the test plot.

7. The apparatus set forth in claim 1, wherein said retaining wall includes means for preventing lateral flow of runoff along said retaining wall.

8. The apparatus set forth in claim 1, wherein said collector assembly further includes a flume equipped with means for measuring runoff flow.

9. The apparatus set forth in claim 8, wherein said runoff collection means further includes a storage reservoir to hold the runoff from the test plot for quantitative analysis.

10. The apparatus set forth in claim 1, wherein said test plot is an area of 0.1 to 1.0 acres.

11. The apparatus set forth in claim 1, wherein said simulated rainfall applying means includes multiple irrigation heads, each said irrigation head including means for regulating water pressure.

12. An apparatus for conducting meso-scale rainfall simulations and runoff collections, comprising:
    means for evenly and continuously applying to a test plot simulated rainfall having a droplet size spectrum, an impact velocity, a spatial uniformity and an intensity/duration similar to natural rainfall whereby a substantially uniform input of water and energy is attained over said test plot, said simulated rainfall applying means including (a) a main pipeline and at least two lateral lines, said main pipeline and lateral lines running along the ground so as to allow the free flow of air and uninterrupted application of sunlight to the test plot and (b) means for pumping water through said main pipeline and at least two lateral lines;
    means for collecting runoff from said test plot for analysis; and
    a drain valve connected to each lateral line, at least one of said drain valves including means for connecting a garden hose.

13. A method for conducting meso-scale rainfall simulations and runoff collections, comprising the steps of:
    selecting a spray means providing a droplet size spectrum closely resembling natural rainfall to be simulated;
    adjusting spacing between said spray means in order to insure spatial uniformity of application of simulated rainfall over a test plot;
    adjusting relative height of said spray means above the ground to insure a droplet velocity at time of impact with the ground closely resembling natural rainfall to be simulated;
    applying said simulated rainfall evenly and continuously at a selected intensity/duration over the test plot so as to provide a substantially uniform input of water and energy;
    collecting runoff from said test plot; and analyzing said runoff that is collected.

14. The method set forth in claim 13, including studying natural rainfall for a geographic area including the test plot in order to determine droplet size spectrum, droplet impact velocity and intensity/duration of a storm having a defined return frequency for said natural rainfall.

15. The method set forth in claim 13, including installing a runoff collection assembly in the ground immediately adjacent a lower end of said test plot so that there is no buffer area of soil between said test plot and said runoff collection assembly.

16. The method set forth in claim 15, wherein said installing step includes excavating ground immediately adjacent said lower end of said test plot and placing said runoff collection assembly in said excavation.

17. The method set forth in claim 16, including providing said runoff collection assembly with an effectively continuous bottom wall impervious to said runoff and converging sidewalls for concentrating said runoff.

* * * * *